US012728185B2

(12) United States Patent
Quach et al.

(10) Patent No.: US 12,728,185 B2
(45) Date of Patent: Sep. 8, 2026

(54) TISSUE-PLASMINOGEN ACTIVATOR COATED CATHETER WITH HYDROGEL-CONTROLLED ELUTION

(71) Applicant: Becton, Dickinson and Company, Franklin Lakes, NJ (US)

(72) Inventors: Christopher Quach, North Salt Lake, UT (US); Dustin Payne, West Jordan, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 586 days.

(21) Appl. No.: 18/207,557

(22) Filed: Jun. 8, 2023

(65) Prior Publication Data

US 2024/0408286 A1 Dec. 12, 2024

(51) Int. Cl.
*A61L 33/00* (2006.01)
*A61L 29/08* (2006.01)
(Continued)

(52) U.S. Cl.
CPC ......... *A61L 33/0064* (2013.01); *A61L 29/085* (2013.01); *A61L 29/145* (2013.01);
(Continued)

(58) Field of Classification Search
CPC .... A61L 33/0064; A61L 33/064; A61L 33/08; A61L 29/085; A61L 29/145; A61L 29/16
See application file for complete search history.

(56) References Cited

U.S. PATENT DOCUMENTS

2003/0114791 A1 6/2003 Rosenthal et al.
2005/0100580 A1 5/2005 Osborne et al.
(Continued)

FOREIGN PATENT DOCUMENTS

WO 2004112851 A1 12/2004
WO 2022021363 A1 2/2022

OTHER PUBLICATIONS

Park Y-J et al: "Controlled release of clot-dissolving tissue-type plasminogen activator from a poly (l-glutamic acid) semi-interpenetrating polymer network hydrogel", Journal of Controlled Release, Elsevier Amsterdam, NL, vol. 75, No. 1-2, Jul. 10, 2001(Jul. 10, 2001), pp. 37-44, xp004254401, ISSN: 0168-3659, DOI: 10.1016/S0168-3659(01)00360-1 the whole document.

*Primary Examiner* — Dung T Ulsh

(74) *Attorney, Agent, or Firm* — Kirton McConkie; Whitney Blair; Kevin Stinger

(57) ABSTRACT

A thrombo-resistant catheter includes a hydrogel coating containing a thrombolytic agent. The thrombolytic agent may be a lyophilized tissue plasminogen activator. The catheter has an intraluminal surface and an extraluminal surface, and the hydrogel coating is disposed on the intraluminal surface and/or the extraluminal surface. The hydrogel coating may have a thickness in the range of about 50 nm to about 150 nm. The hydrogel coating may contain from about 0.1 wt. % to about 1 wt. % tissue plasminogen activator. The hydrogel coating may be made of a synthetic hydrogel or a natural hydrogel. Presently preferred synthetic hydrogels include polyacrylamide-based hydrogels. Presently preferred natural hydrogels include hyaluronic acid-based hydrogels. The hydrogel coating reacts in the presence of a physiological fluid to absorb water and elute the thrombolytic agent. The hydrogel controls elution of the thrombolytic agent. Examples of physiological fluid include interstitial fluid and blood.

6 Claims, 3 Drawing Sheets

(51) Int. Cl.

| | |
|---|---|
| ***A61L 29/14*** | (2006.01) |
| ***A61L 29/16*** | (2006.01) |
| ***A61L 33/06*** | (2006.01) |
| ***A61L 33/08*** | (2006.01) |

(52) U.S. Cl.

CPC ............. *A61L 29/16* (2013.01); *A61L 33/064* (2013.01); *A61L 33/08* (2013.01); *A61L 2300/42* (2013.01)

(56) References Cited

U.S. PATENT DOCUMENTS

| | | | |
|---|---|---|---|
| 2014/0171864 A1 | 6/2014 | Michal et al. | |
| 2016/0058913 A1 | 3/2016 | Dimitrievska et al. | |
| 2021/0016318 A1* | 1/2021 | Lam ....................... | B05D 7/225 |

* cited by examiner

TISSUE-PLASMINOGEN ACTIVATOR COATED CATHETER WITH HYDROGEL-CONTROLLED ELUTION

BACKGROUND

The disclosure relates to catheters comprising a thrombolytic coating to provide inherent thrombo-resistant properties. The disclosure also relates to thrombo-resistant catheters coated with a hydrogel containing a thrombolytic agent. The hydrogel provides controlled elution of the thrombolytic agent. The thrombolytic agent may be a tissue plasminogen activator.

Intravenous catheters are life saving devices that have become a standard of care. For example, peripheral intravenous catheters (PIVCs) are often used in acute applications such as short-inpatient and outpatient services. Alternatively, peripherally inserted central catheters (PICCs) are used in chronic/long-duration applications.

When catheters, or other biomedical devices, contact blood for a prolonged period, the process of thrombosis initiates. Adsorption of proteins is one of the first events to occur when blood contacts a foreign surface. The compositions and conformation of adsorbed proteins influence subsequent cellular responses such as platelet adhesion, aggregation, secretion, complement activation, and ultimately, the formation of cross-linked fibrin and thrombus. In addition to thrombus formation, biofilm formation and bacterial infection can occur.

State of the art anti-platelet/anti-thrombogenic technologies generally employ surface modification techniques to delay protein adhesion or heparin-based technologies.

State-of-the-art anti-platelet and anti-thrombogenic technologies are generally ineffective for long periods of time (greater than 7 days in blood stream) since they try to prevent protein adhesion, which is a complicated phenomenon that generally overcomes all surface modification techniques. While heparin technologies are more successful, they are extremely expensive and difficult for scale-up in rapid throughput manufacturing scenarios.

Accordingly, there is a need in the art for catheters having improved anti-platelet and anti-thrombogenic capabilities. Such catheters are disclosed herein.

The subject matter claimed herein is not limited to embodiments that solve any disadvantages or that operate only in environments such as those described above. Rather, this background is only provided to illustrate one example technology area where some implementations described herein may be practiced.

SUMMARY

The present invention has been developed in response to problems and needs in the art that have not yet been fully resolved by currently available thrombo-resistant catheters. The disclosed catheters provide inherent thrombo-resistant properties.

One general aspect includes a catheter with inherent thrombo-resistant properties having an extruded catheter body which comprises a hydrogel coating comprising a thrombolytic agent. The catheter body may include an intraluminal surface and an extraluminal surface. A hydrogel coating may be disposed on the intraluminal surface and/or the extraluminal surface, wherein the hydrogel coating comprises a thrombolytic agent.

The catheter may be a peripheral intravenous catheter (PIVC). The catheter may be a peripherally inserted central catheter (PICC). The catheter may be a urinary catheter. The catheter may be a dialysis catheter, including acute and chronic dialysis catheters, and peritoneal dialysis catheters. The catheter may be any other catheter introduced into a body lumen.

Implementations may include one or more of the following features.

In some nonlimiting embodiments, the thrombolytic agent includes a tissue plasminogen activator. The tissue plasminogen activator may be lyophilized. In some embodiments, the hydrogel coating comprises from about 0.1 wt. % to about 1 wt. % tissue plasminogen activator.

In some embodiments, the hydrogel coating comprises a natural hyaluronic acid hydrogel. In some nonlimiting embodiments, the hydrogel coating comprises a synthetic hydrogel. Nonlimiting examples of synthetic hydrogels includes synthetic polyacrylamide hydrogels. One advantage of synthetic hydrogels is that they can be prepared as a liquid prepolymerization mixture, applied to a catheter surface as a layer or coating, and then polymerized on the surface to provide a desired hydrogel coating. In some embodiments, the hydrogel coating has a thickness in the range of about 50 nm to about 150 nm.

In some nonlimiting embodiments, the hydrogel coating reacts in the presence of a physiological fluid to elute the thrombolytic agent. The hydrogel coating slowly absorbs water upon exposure to physiological fluid. In the case of the thrombolytic agent comprising lyophilized tPA, the water reacts with the tPA to reconstitute the tPA and permit the tPA to elute from the catheter surface and initiate fibrin breakdown in thrombus at or near the catheter surface. The rate at which the hydrogel absorbs water from physiological fluids affects the elution rate of the thrombolytic agent. The hydrogel provides controlled elution of the thrombolytic agent. The physiological fluid is selected from interstitial fluid and blood.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
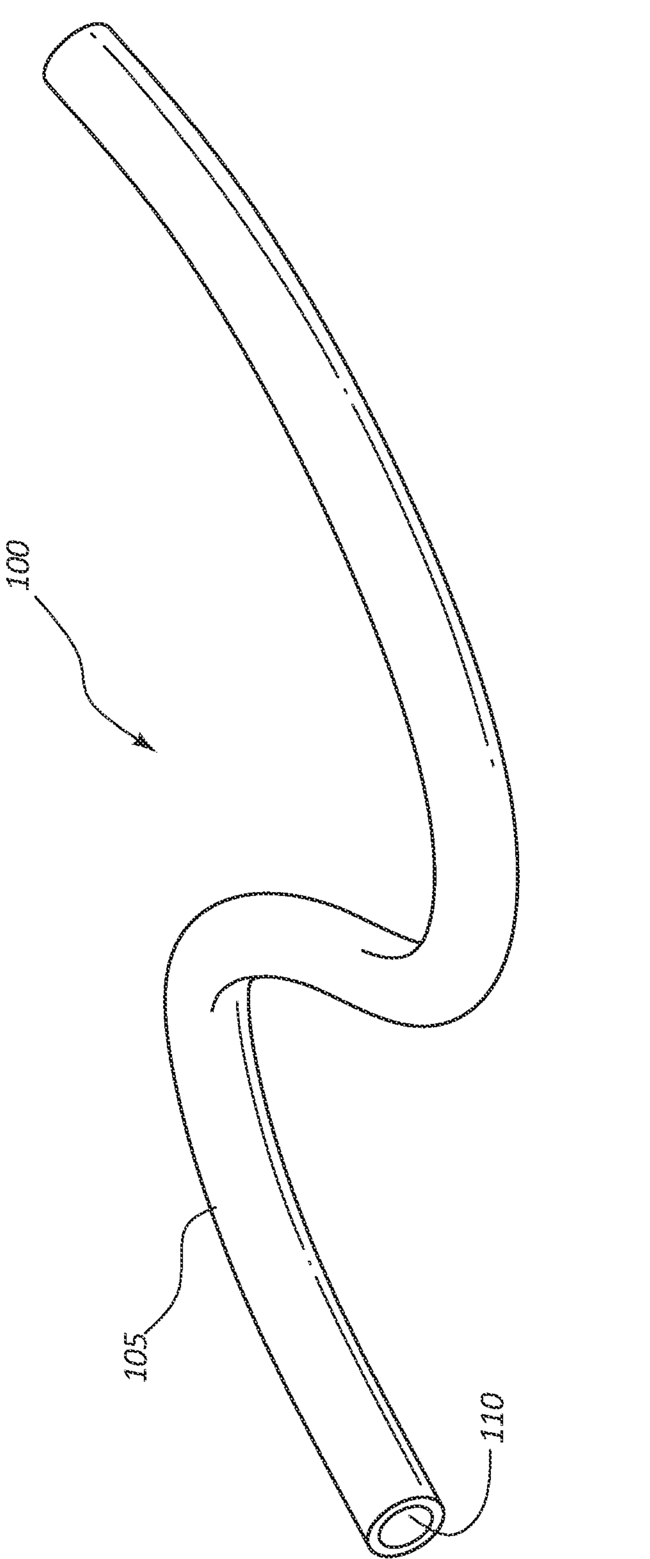
FIG. 1 is a perspective view of an extruded catheter body.

The disclosure relates to catheters comprising a thrombolytic coating to provide inherent thrombo-resistant properties. In some disclosed embodiments, the catheters are coated with a hydrogel coating containing a thrombolytic agent. In some disclosed embodiments, the thrombolytic agent is a tissue plasminogen activator. In some disclosed embodiments, the tissue plasminogen activator is lyophilized.

The hydrogel coating reacts in the presence of a physiological fluid to elute the thrombolytic agent. In some embodiments, the physiological fluid is selected from interstitial fluid and blood. Upon exposure to physiological fluid, the hydrogel slowly hydrates. As the hydrogel hydrates, the lyophilized tissue plasminogen activator reconstitutes and is slowly eluted. The tissue plasminogen activator breaks down thrombus as it forms at or near hydrogel coating on the catheter surfaces. The hydrogel coating provides controlled elution of the tissue plasminogen activator.

Tissue plasminogen activator (tPA) is a protein involved in the breakdown of blood clots. It is a serine protease found on endothelial cells, the cells that line the blood vessels. As an enzyme, it catalyzes the conversion of plasminogen to plasmin, the major enzyme responsible for clot breakdown.

As used herein tPA includes tPA-based thrombolytic drugs. There are many forms of tPA-based thrombolytic drugs currently used in cases of acute myocardial infarction, cerebrovascular thrombotic stroke, and pulmonary embolism, and include:

Alteplase, sold under the brand name Activase among others, is a biosynthetic form of human PA. It is a 527-amino-acid tPA produced by recombinant DNA technology from a human melanoma cell line.

Reteplase, sold under the trade name Retavase, is a genetically engineered, smaller derivative of recombinant tPA that has increased potency and is faster acting than recombinant tPA.

Tenecteplase is a genetically engineered variant of Alteplase.

Streptokinase and Anistreplase are isolated and purified from streptococci bacteria production. They mimic endogenous tPA. Streptokinase is one of the leading and one of the most-often employed, due to its lower cost. Anistreplase (Eminase) is a complex of streptokinase and plasminogen. Both are used in acute myocardial infarction, arterial and venous thrombosis, and pulmonary embolism.

It is desirable to use tPA as a lyophilized powder. As an example, lyophilized tPA is available from Genentech, San Francisco, CA. Reconstituted tPA exhibits full activity for about 8 hours after reconstitution in sterile water at room temperature.

The tPA is incorporated in a hydrogel coating. Various biocompatible hydrogel materials may be used, including, but not limited to, synthetic polyacrylamide-based hydrogels and natural hyaluronic acid-based hydrogels.

A variety of synthetic polyacrylamide-based polymer and copolymer hydrogels may be prepared from acrylamide monomers and mixtures thereof. Suitable acrylamide monomers include, but are not limited to, acrylamide, dimethylacrylamide; diethylacrylamide; hydroxymethylacrylamide; hydroxyethylacrylamide; methoxypropylacrylamide; N-[tris(hydroxymethyl)methyl]acrylamide; 4-acryloylmorpholine; N-[3-(dimethylamino)propyl]-methylacrylamide; (acrylamidopropyl)trimethylammonium; 2-acrylamino-2-methyl-propane sulfonic acid; N-isopropylacrylamide. Hydrogels can be prepared by photo-polymerization in UV light using a radical photoinitiator. Lithium phenyl-2,4,6-trimethylbenzoylphosphinate (LAP) is one example of a radical photoinitiator. A simple UV LED ($\lambda$=350 to 365 nm) may provide a UV light source.

In an embodiment, a quantity of thrombolytic agent, such as tPA and preferably lyophilized tPA, is combined with one or more acrylamide monomers to form a prepolymer solution. A radical photoinitiator is also included in the prepolymer solution. A catheter body is dipped into the prepolymer solution according to conventional catheter dip coating techniques to coat the catheter with a thin layer of the prepolymer solution on intraluminal and/or extraluminal surfaces of the catheter. One method of coating intraluminal surfaces includes dipping the distal end of the catheter into the hydrogel prepolymer solution comprising the thrombolytic agent and applying a vacuum to the proximal end of the lumen or lumens to draw the prepolymer solution within the lumen or lumens. Upon removal of the catheter from the prepolymer solution, the hydrogel coating may be photopolymerized by applying UV light, of about 350 to 365 nm, for sufficient time to cause polymerization. In some embodiments, the photopolymerization exposure time is between about 10 seconds and 1 minute.

In some embodiments, the hydrogel coating has a thickness in the range from 50 to 150 nm.

One advantage of the hydrogel coatings disclosed herein is that the hydrogel coating absorbs water present in physiological fluid. As water slowly penetrates the hydrogel coating, the water permits elution of the thrombolytic agent. In embodiments where the thrombolytic agent comprises tPA, the water reacts with and reconstitutes the tPA. The reconstituted and active tPA elutes to the surface of the hydrogel coating on catheter to initiate fibrin breakdown in thrombus located at or near the catheter surface. The physiological fluid is selected from interstitial fluid and blood.

The catheter body may be prepared by conventional polymer extrusion processes. Non-limiting examples of typical catheter body polymeric materials include common thermoplastic elastomers, such as polyethylene (PE), including low density polyethylene ("LDPE"), linear low density polyethylene ("LLDPE"), high density polyethylene ("HDPE") and blends thereof, polypropylene (PP), polyvinyl chloride (PVC), polyurethane (TPU), polytetrafluoroethylene (PTFE), and ethylene vinyl acetate (EVA).

Medical grade thermoplastic polyurethane (TPU) is a presently preferred polymeric material used to manufacture the catheter body. Nonlimiting examples of medical grade TPUs include the polyether and polyester-based thermoplastic polyurethanes (TPUs) sold by Biomerics under the tradename Quadraflex™; the polycarbonate-based TPUs sold by Biomerics under the tradename Quadrathane™; the aromatic rigid TPUs sold by Biomerics under the tradename Quadraplast™; the thermoplastic silicone polyurethane copolymers sold by Biomerics under the tradename Quadrasil™; the antimicrobial TPUs sold by Biomerics under the tradename Quadraban™; the aliphatic, hydrophilic thermoplastic polyurethanes sold by Biomerics under the tradename Quadraphlic™; and the engineered TPUs sold by Lubrizol under the tradename Isoplast™.

The disclosed catheters may be used in a variety of different medical applications. In some embodiments, the catheter is a peripheral intravenous catheter (PIVC). In some embodiments, the catheter is a peripherally inserted central catheter (PICC).

In some embodiments, the catheter is a urinary catheter. Non-limiting examples of urinary catheters include indwelling urinary catheters such as Foley catheters; external catheters such as the PureWick™ female external catheter from C. R. Bard, Inc.; and intermittent urinary catheters, with and without lubricious coatings, including the Magic³ GO™ intermittent catheter also from C. R. Bard, Inc.

In some embodiments, the catheter is a dialysis catheter, including acute and chronic dialysis catheters, and peritoneal dialysis catheters. In some embodiments, the catheter is a catheter introduced into a body lumen.

FIG. 1 depicts a portion of a catheter 100 fabricated of a conventional polymer material having a hydrogel coating selected to provide thrombo-resistant properties. As shown therein, at least a portion of the catheter 100 may be formed by extrusion of a polymeric matrix. The catheter 100 includes an extruded catheter body 105. As shown in FIG. 1, the catheter 100 may, also include a lumen 110 extending through at least a portion of the catheter body 105. While not shown in FIG. 1, the catheter 100 may include more than one lumen extending through at least a portion of the catheter body 105.

Figure 2A:
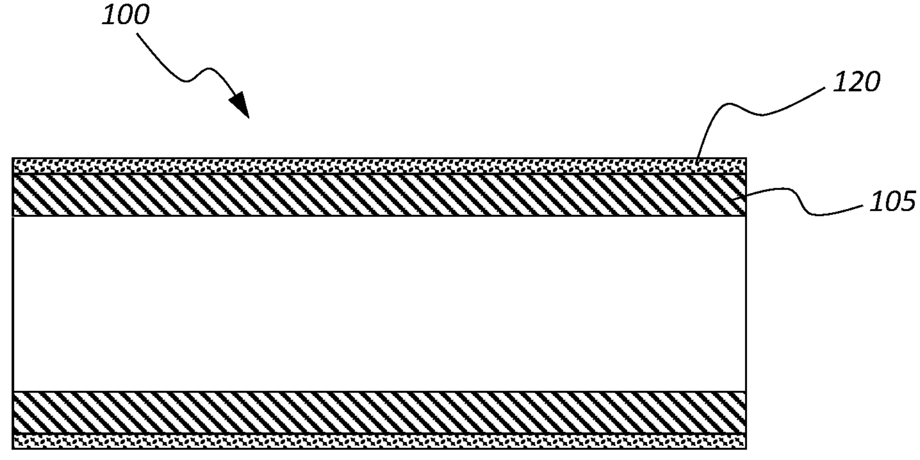
FIG. 2A is a cross-sectional representation of a portion of a catheter body with an intraluminal surface having a hydrogel coating which comprises a thrombolytic agent to provide thrombo-resistant properties.

It will further be appreciated that the shape and/or size of the catheter 100 can be varied as desired. For example, various shapes and/or sizes of extrusion dies can be used to form catheters having particular shapes and/or sizes. Accordingly, it will be understood that the embodiment of FIG. 1 is merely exemplary of one type of extruded catheter, FIG. 2A is a cross-sectional representation of portion of a catheter 100 having a catheter body 105 fabricated of conventional polymer material. The catheter further includes a layer 120 on the catheter body 105. The layer 120 comprises a hydrogel coating comprising a thrombolytic agent, such as tPA. In the embodiment shown in FIG. 2A the layer 120 is disposed on an extraluminal surface of the catheter body 105.

The layer 120 may be made by a coating process, such as dip coating described above.

Figure 2B:
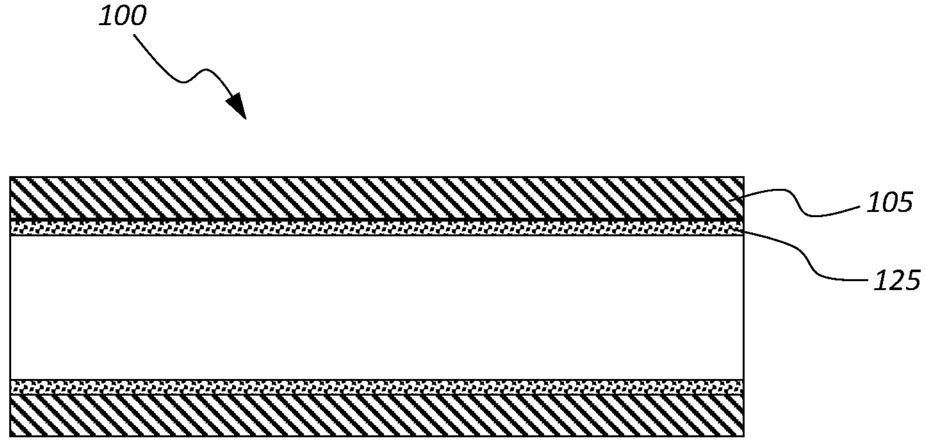
FIG. 2B is a cross-sectional representation of a portion of a catheter body with an extraluminal surface having a hydrogel coating which comprises a thrombolytic agent to provide thrombo-resistant properties.

FIG. 2B is a cross-sectional representation of portion of a catheter 100 having a catheter body 105 fabricated of conventional polymer material. The catheter further includes a layer 125 on the catheter body 105. The layer 125 comprises a hydrogel coating comprising a thrombolytic agent, such as tPA. In the embodiment shown in FIG. 2B the layer 125 is disposed on an intraluminal surface of the catheter body 105.

The layer 125 may be made by a coating process, such as dip coating described above.

Figure 2C:
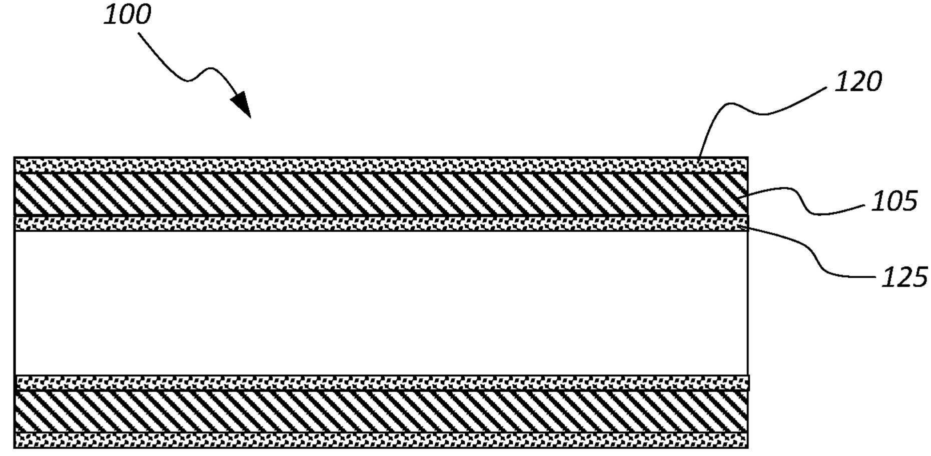
FIG. 2C is a cross-sectional representation of a portion of a catheter body with an intraluminal and an extraluminal surface having a hydrogel coating which comprises a thrombolytic agent to provide thrombo-resistant properties.

FIG. 2C is a cross-sectional representation of portion of a catheter 100 having a catheter body 105 fabricated of conventional polymer material. The catheter further includes a layer 120 on the catheter body 105. The layer 120 comprises a hydrogel coating comprising a thrombolytic agent, such as tPA. The catheter further includes a layer 125 on the catheter body 105. The layer 125 comprises a hydrogel coating comprising a thrombolytic agent, such as tPA. In the embodiment shown in FIG. 2C the layer 120 is disposed on an extraluminal surface of the catheter body 105. In the embodiment shown in FIG. 2C the layer 125 is disposed on an intraluminal surface of the catheter body 105.

EMBODIMENTS

Various embodiments are listed below. It will be understood that the embodiments listed below may be combined with all aspects and other embodiments in accordance with the scope of the invention.

Embodiment 1. A thrombo-resistant catheter comprising a hydrogel coating, wherein the hydrogel coating comprises a thrombolytic agent.

Embodiment 2. The catheter of Embodiment 1, wherein the thrombolytic agent comprises a tissue plasminogen activator.

Embodiment 3. The catheter of Embodiment 2, wherein the tissue plasminogen activator is lyophilized.

Embodiment 4. The catheter of any preceding Embodiment, wherein the hydrogel coating comprises from about 0.1 wt. % to about 1 wt. % tissue plasminogen activator.

Embodiment 5. The catheter of any preceding Embodiment, wherein the hydrogel coating comprises a synthetic polyacrylamide hydrogel.

Embodiment 6. The catheter of any of Embodiments 1 through 4, wherein the hydrogel coating comprises a natural hyaluronic acid hydrogel.

Embodiment 7. The catheter of any preceding Embodiment, wherein the hydrogel coating has a thickness in the range of about 50 nm to about 150 nm.

Embodiment 8. The catheter of any preceding Embodiment, wherein the hydrogel coating reacts in the presence of a physiological fluid to elute the thrombolytic agent.

Embodiment 9. The catheter of Embodiment 8, wherein the physiological fluid is selected from interstitial fluid and blood.

Embodiment 10. The catheter of any preceding Embodiment, wherein the catheter comprises an intraluminal surface and an extraluminal surface, and wherein the hydrogel coating is disposed on the intraluminal surface and the extraluminal surface.

Embodiment 11. A thrombo-resistant catheter comprising: an intraluminal surface and an extraluminal surface; and a hydrogel coating disposed on the intraluminal surface and the extraluminal surface, wherein the hydrogel coating comprises a lyophilized tissue plasminogen activator.

Embodiment 12. The catheter of Embodiment 11, wherein the tissue plasminogen activator has a concentration in the hydrogel coating from about 0.1 wt. % to about 1 wt. %.

Embodiment 13. The catheter of Embodiments 11 or 12, wherein the hydrogel coating comprises a synthetic polyacrylamide hydrogel.

Embodiment 14. The catheter of Embodiments 11 or 12, wherein the hydrogel coating comprises a natural hyaluronic acid hydrogel.

Embodiment 15. The catheter of any of the Embodiments 11 through 14, wherein the hydrogel coating has a thickness in the range of about 50 nm to about 150 nm.

Embodiment 16. The catheter of any of the Embodiments 11 through 15, wherein the hydrogel coating reacts in the presence of a physiological fluid to reconstitute and elute the tissue plasminogen activator.

Embodiment 17. The catheter of Embodiment 16, wherein the physiological fluid is selected from interstitial fluid and blood.

Embodiment 18. The catheter of any of the Embodiments 11 through 17, wherein the tissue plasminogen activator has a concentration in the hydrogel coating from about 0.1 wt. % to about 1 wt. %., the hydrogel coating has a thickness in the range of about 50 nm to about 150 nm, and the hydrogel coating comprises a synthetic polyacrylamide hydrogel.

Embodiment 19. The catheter of Embodiment 18, wherein the hydrogel coating rehydrates in the presence of a physiological fluid to reconstitute and elute the tissue plasminogen activator.

Embodiment 20. The catheter of Embodiment 19, wherein the physiological fluid is selected from interstitial fluid and blood.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, the various changes, substitutions, and alterations could be made hereto without departing from the spirit and scope of the invention. It should be understood that the embodiments may be combined.

The invention claimed is:

1. A thrombo-resistant catheter comprising:

an intraluminal surface and an extraluminal surface; and a dehydrated hydrogel coating disposed on the intraluminal surface and the extraluminal surface, wherein the hydrogel coating comprises a lyophilized tissue plasminogen activator, wherein the hydrogel coating rehydrates in the presence of a physiological fluid to reconstitute and elute the tissue plasminogen activator, wherein the physiological fluid is selected from interstitial fluid and blood.

2. The catheter of claim 1, wherein the tissue plasminogen activator has a concentration in the hydrogel coating from about 0.1 wt. % to about 1 wt. %.

3. The catheter of claim 1, wherein the hydrogel coating comprises a synthetic polyacrylamide hydrogel.

4. The catheter of claim 1, wherein the hydrogel coating comprises a natural hyaluronic acid hydrogel.

5. The catheter of claim 1, wherein the hydrogel coating has a thickness in the range of about 50 nm to about 150 nm.

6. A thrombo-resistant catheter comprising:

an intraluminal surface and an extraluminal surface; and a dehydrated hydrogel coating disposed on the intraluminal surface and the extraluminal surface, wherein the hydrogel coating comprises lyophilized tissue plasminogen activator, wherein the tissue plasminogen activator has a concentration in the hydrogel coating from about 0.1 wt. % to about 1 wt. %., the hydrogel coating has a thickness in the range of about 50 nm to about 150 nm, and the hydrogel coating comprises a synthetic polyacrylamide hydrogel, wherein the hydrogel coating rehydrates in the presence of a physiological fluid to reconstitute and elute the tissue plasminogen activator, wherein the physiological fluid is selected from interstitial fluid and blood.

* * * * *